US012561490B2

(12) United States Patent
Rodriguez Leon et al.

(10) Patent No.: US 12,561,490 B2
(45) Date of Patent: Feb. 24, 2026

(54) ADAPTATION OF THE ADVANCED PENG ROBINSON EQUATION OF STATE BASED ON A MOLECULAR STRUCTURE BASIS FOR MODELING THE ASPHALTENE PRECIPITATION OF PETROLEUM FLUIDS

(71) Applicant: Schlumberger Technology Corporation, Sugar Land, TX (US)

(72) Inventors: Sandra Rodriguez Leon, Calgary (CA); Glen Andrew Hay, Calgary (CA); Kurt Andreas George Schmidt, Calgary (CA)

(73) Assignee: Schlumberger Technology Corporation, Sugar Land, TX (US)

( * ) Notice: Subject to any disclaimer, the term of this patent is extended or adjusted under 35 U.S.C. 154(b) by 1208 days.

(21) Appl. No.: 17/248,761

(22) Filed: Feb. 5, 2021

(65) Prior Publication Data

US 2022/0253580 A1     Aug. 11, 2022

(51) Int. Cl.
| | |
|---|---|
| *G01N 33/48* | (2006.01) |
| *G01N 33/50* | (2006.01) |
| *G06F 30/12* | (2020.01) |
| *G16C 20/30* | (2019.01) |
| *G06F 111/10* | (2020.01) |
| *G06F 113/08* | (2020.01) |

(52) U.S. Cl.
CPC ............. *G06F 30/12* (2020.01); *G16C 20/30* (2019.02); *G06F 2111/10* (2020.01); *G06F 2113/08* (2020.01)

(58) Field of Classification Search
CPC .. G06F 30/12; G06F 2111/10; G06F 2113/08; G06F 2119/08; G06F 30/28; G16C 20/30
See application file for complete search history.

(56) References Cited

U.S. PATENT DOCUMENTS

2020/0095898 A1 *   3/2020   Hossain .................... F02C 6/18

FOREIGN PATENT DOCUMENTS

WO      WO-2018208360 A2 * 11/2018   ......... G06F 16/2379

OTHER PUBLICATIONS

Soave G. Equilibrium constants from a modified Redlich-Kwong equation of state. Chemical Engineering Science, vol. 27, pp. 1197-1203. (Year: 1972).*
Abutaqiya et al. Accurate modeling of asphaltene inset pressure in crude oils under gas injection using Peng-Robinson equation of state. Energy & Fuels, vol. 34, Mar. 2, 2020, pp. 4055-4070. (Year: 2020).*

Abutaqiya et al. Aromatic Ring Index (ARI): A characterization factor for nonpolar hydrocarbons from molecular weight and refractive index. Energy & Fuels, vol. 35, Jan. 11, 2021, pp. 1113-1119. (Year: 2021).*
Groenzin et al. Molecular size and structure of asphaltenes from various sources. Energy & Fuels, vol. 14, pp. 677-684. (Year: 2000).*
Kajiyama et al. Improved synthesis with high yield and increased molecular weight of poly(alpha,beta-malic acid) by direct polycondensation. Biomacromolecules, vol. 5, pp. 169-174. (Year: 2004).*
Arya, A., et al "Determination of asphaltene onset conditions using the cubic plus association equation of state". Fluid Phase Equilibria 400, 2015, 8-19.
Gholoum, EF et al, "Investigation of asphaltene precipitation onset conditions for Kuwait reservoir". Society of Petroleum Engineers SPE, 81571, 2003.
Gonzalez, DL., et al., "Effects of Gas Additions to Deepwater Gulf of Mexico Reservoir Oil: Experimental Investigation of Asphaltene Precipitation and Deposition". Society of Petroleum Engineers (SPE) 159098, 2012.
Arya, A., et al "Predicting of Gas Injection Effect on Asphaltene Precipitation Onset Using the Cubic and Cubic-Plus-Association Equations of State". Energy and Fuels 31, 2017, 3313- 3328.
Panuganti, S.R., et al "SAFT model for upstream asphaltene applications". Fluid Phase Equilibria 359, 2013, 2-16.
Jamaluddin, et al, "An Investigation of Asphaltene Instability Under Nitrogen Injection". Society of Petroleum Engineers (SPE) 74393, 2002.
Bahrami, P., et al "Prediction of the Gas Injection Effect on the Asphaltene Phase Envelope". Oil & Gas Science and Technology—Rev. IFP Energies Nouvelles vol. 70, 2015, 1075-1086.
Canas-Marin, W.A., et al "A theoretically modified PC-SAFT equation of state for predicting asphaltene onset pressures at low temperatures". Fluid Phase Equilibria 495, 2019, 1-11.
Punnapala, S., et al "Revisiting the PC-SAFT characterization procedure for an improved asphaltene precipitation prediction". Fuel 108, 2012, 417-429.

(Continued)

*Primary Examiner* — Russell S Negin
(74) *Attorney, Agent, or Firm* — Jeffrey D. Frantz

(57)          ABSTRACT

Fluid modeling methods and systems are provided for predicting phase behavior of petroleum fluids using a computational model that employs pseudo-components of varying carbon numbers that represent asphaltenes, asphaltene-like hydrocarbon, and non-asphaltene hydrocarbons. The computational model models the phase equilibria of the mixture of components with mixing rules that employ binary interaction parameters determined from correlations that involve certain properties or parameters associated with respective pseudo-component pairs as input variables. The binary interaction parameters are tuned by adjusting at least one parameter of the respective correlations based on matching at least one measured property of one or more petroleum fluids to a corresponding property predicted by the computational model for the one or more petroleum fluids. The tuned values for the binary interaction parameters can be stored as part of the computational model for subsequent fluid modeling. In embodiments, the computational model is based on the Advanced Peng Robinson equation of state.

23 Claims, 12 Drawing Sheets

(56) References Cited

OTHER PUBLICATIONS

Fahim, M.A. "Empirical Equations for Estimating ADE of Crude Oils". Petroleum Science and Technology 25:7, 2007, 949-965.
Hay, G., et al "Thermodynamic Modeling and Process Simulation through PIONA characterization". Energy & Fuels 27 (6), 3578-3584.

* cited by examiner

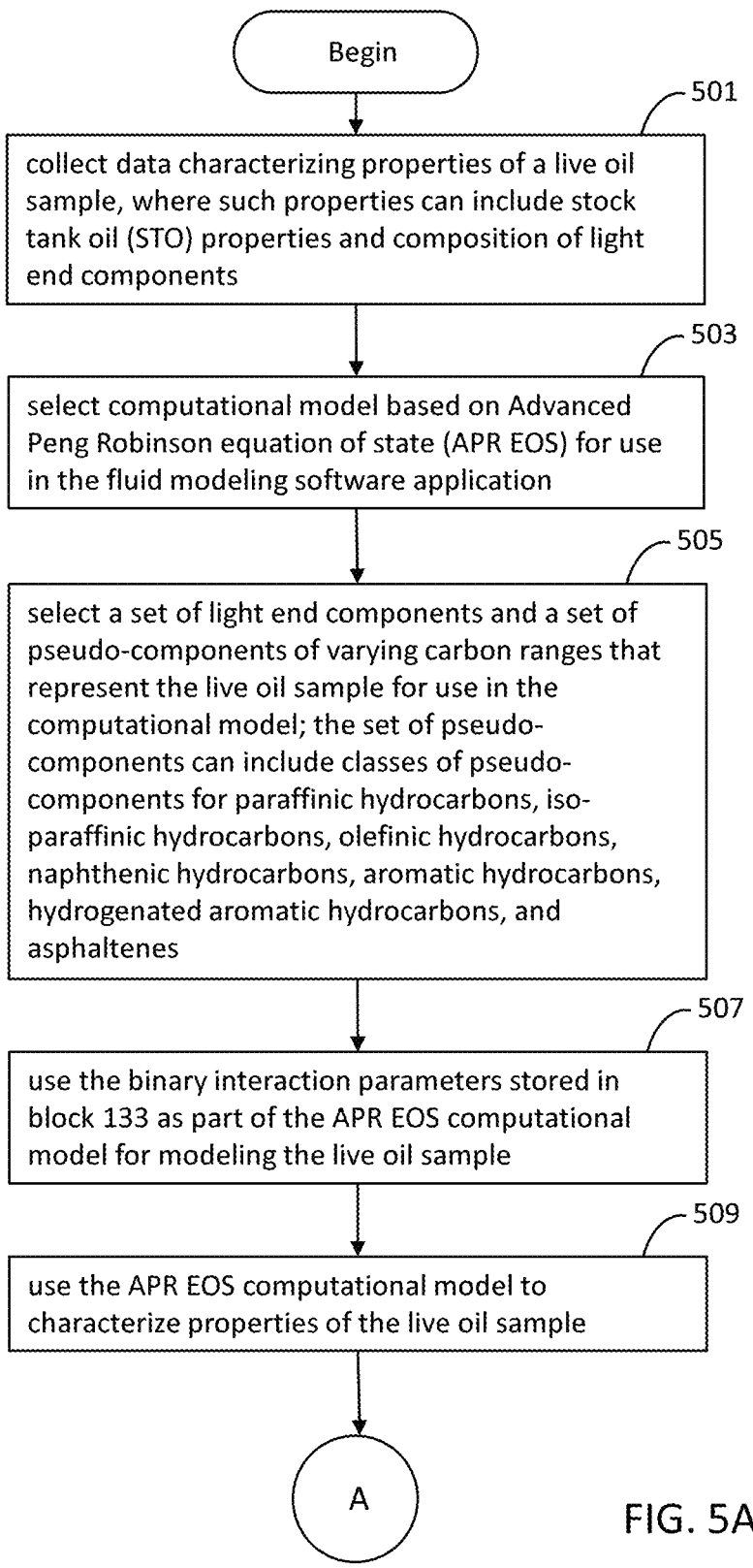

Begin collect data characterizing properties of a live oil sample, where such properties can include stock tank oil (STO) properties and composition of light end components

501 select computational model based on Advanced Peng Robinson equation of state (APR EOS) for use in the fluid modeling software application

503 select a set of light end components and a set of pseudo-components of varying carbon ranges that represent the live oil sample for use in the computational model; the set of pseudo-components can include classes of pseudo-components for paraffinic hydrocarbons, iso-paraffinic hydrocarbons, olefinic hydrocarbons, naphthenic hydrocarbons, aromatic hydrocarbons, hydrogenated aromatic hydrocarbons, and asphaltenes

505 use the binary interaction parameters stored in block 133 as part of the APR EOS computational model for modeling the live oil sample

507 use the APR EOS computational model to characterize properties of the live oil sample

ADAPTATION OF THE ADVANCED PENG ROBINSON EQUATION OF STATE BASED ON A MOLECULAR STRUCTURE BASIS FOR MODELING THE ASPHALTENE PRECIPITATION OF PETROLEUM FLUIDS

FIELD

The present application relates to computer-based methods and systems that model and predict phase behavior of petroleum fluids (e.g., crude oils) due to changes in temperature, pressure, and composition.

BACKGROUND

Petroleum fluids (e.g., crude oils) typically include a number of constituent components or fractions each having a particular molecular composition, molecular weight, and boiling point. One or more of the fractions can be divided into several pseudo-components of varying molecular composition, molecular weight, and boiling point. For example, asphaltenes are the heaviest and most polar fraction of petroleum fluids and consist of polynuclear aromatic hydrocarbons with high content of metals and heteroatoms. Asphaltenes are typically divided into several pseudo-components representing polynuclear aromatic hydrocarbons with varying molecular composition with possible metals and heteroatoms, such as nitrogen (N), sulfur (S), vanadium (V), nickel (Ni), and iron (Fe). Petroleum fluids can also include an asphaltene-like fraction that consist of aromatic and dehydrogenated aromatic hydrocarbons. This asphaltene-like fraction is typically divided into several pseudo-components representing aromatic and dehydrogenated aromatic hydrocarbons of varying molecular composition, molecular weight, and boiling point.

Understanding the phase behavior of the asphaltene fraction as well as the asphaltene-like fraction of petroleum fluids in both the upstream and downstream processing is important because the asphaltene and asphaltene-like fractions tend to precipitate upon changes in temperature, pressure, and composition. This precipitation phenomena causes serious operational problems such as reservoir formation damage, plugging of production equipment and pipelines, all of which can result in a detrimental effect on the production and transport of crude oil.

In order to predict flow assurance issues caused by the precipitation of the asphaltene and asphaltene-like fractions of petroleum fluids, fluid simulation software applications have been developed that utilize computational models that combine the well-known Cubic-Plus-Association equation of state (EOS) and the Perturbed Chain form of the Statistical Associating Fluid Theory (PC-SAFT) to predict the phase behavior of asphaltene and asphaltene-like fractions of petroleum fluids. Even though these computational models have shown promising results in the prediction of the onset of precipitation, their parameters must be individually tuned for each type of fluid indicating that they cannot completely represent the asphaltene precipitation phenomena when the chemical nature of the crude oil changes.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

The present disclosure provides for development and configuration of a fluid simulation software application and related computer-based methods and systems for modeling and predicting the phase behavior of petroleum fluids (e.g., crude oils) using a computational model based on an adaptation of the Advanced Peng Robinson (APR) equation of state (EOS), which is less complex than the Cubic-Plus-Association equation of state (EOS) and the Perturbed Chain of the Statistical Associating Fluid Theory (PC-SAFT) that is typically used for these purposes. The computational model based on the adaptation of the APR EOS, which is referred to herein as an APR EOS computational model, employs a set of pseudo-components of varying carbon number that represent the asphaltene fraction and possibly a set of pseudo-components of varying carbon number and molecular structure (e.g., aromatics, and dehydrogenated aromatics) that represent the asphaltene-like fraction. The maltenes (non-asphaltene or asphaltene-like hydrocarbons) are represented by a set of light end components as well as a set of pseudo-components of varying carbon number and molecular structure for non-asphaltene hydrocarbons (e.g., paraffins, isoparaffins, olefins, and naphthenes). The APR EOS computational model models the phase equilibria of the mixture of the light end components, the pseudo-components for non-asphaltene hydrocarbons, the pseudo-components for asphaltene-like hydrocarbons, and the pseudo-components for asphaltenes with mixing rules that employ binary interaction parameters.

In embodiments, the binary interaction parameters of the APR EOS computational model can include binary interaction parameters between the pseudo-components that represent asphaltenes and the pseudo-components that represent the asphaltene-like hydrocarbons, binary interaction parameters between the pseudo-components that represent asphaltenes and the pseudo-components that represent the non-asphaltene hydrocarbons as well as binary interaction parameters between the pseudo-components for the asphaltenes. These binary interaction parameters are associated with respective pseudo-component pairs and are determined from a generalized set of correlations that involve certain properties or parameters associated with respective pseudo-component pairs as input variables. For example, the correlations can include: two carbon numbers for the two pseudo-components of each pseudo-component pair; two critical properties, such as critical volume, for the two pseudo-components of each pseudo-component pair; and a specific constant parameter value labeled $A_k$ for each pseudo-component pair. In this case, the correlations are independent of fluid temperature.

Additionally or alternatively, the binary interaction parameters of the APR EOS computational model can include binary interaction parameters between the pseudo-components that represents asphaltenes and the light end components. These binary interaction parameters are associated with respective pseudo-component: light end component pairs and are determined from another generalized set of correlations that involve certain properties or parameters associated with respective pseudo-component: light end component pairs as input variables. For example, the correlations can include: two carbon numbers for the asphaltenic pseudo-component and the light end component of each pair; a specific constant parameter value labeled $A_k$ for each pair; and a temperature value. In this case, the correlations are dependent on fluid temperature.

Advantageously, the APR EOS computational model can account for the molecular interaction and different solubility effects of each non-asphaltene hydrocarbon family (e.g., paraffins, isoparaffins, olefins, naphthenes) and each asphaltene-like family (e.g., aromatics, or aromatics dehydrogenated) on the precipitation of the asphaltenes because the binary interaction parameters are estimated according to carbon number and type of molecular structure.

Furthermore, the values of parameters (e.g., specific constant parameters $A_k$) of the correlations that are used to determine the binary interaction parameters of the APR EOS computational model can be adjusted and tuned by an iterative process that uses the APR EOS computational model to predict asphaltene onset pressure as a function of temperature for a number of oil samples (e.g., black oil samples) and adjusts the parameters (e.g., specific constant parameters $A_k$) such that the predicted asphaltene onset pressure matches or corresponds to measured asphaltene onset pressure as a function of temperature for the number of oil samples by satisfying a predetermined matching criterion or criteria. The final tuned values of the parameters (e.g., specific constant parameters $A_k$) can be used as input to the correlations to determine final values of the binary interaction parameters for the APR EOS computational model. The final values of the binary interaction parameters can be stored in electronic form, for example as constants, and accessed for application in subsequent modeling where the asphaltene onset condition or other property of a new live oil sample needs to be determined. This simplifies or eliminates tuning of the computational model, which is an outstanding improvement compared to the CPA and SAFT models. Instead, when tuning is required, the molecular weight distribution of the asphaltene pseudo-components of the new live sample can be tuned such the APR EOS computational model predicts asphaltene onset pressure as a function of temperature for the new live oil sample that matches or corresponds to measured asphaltene onset pressure as a function of temperature for the new live oil sample.

BRIEF DESCRIPTION OF THE DRAWINGS

The subject disclosure is further described in the detailed description which follows, in reference to the noted plurality of drawings by way of non-limiting examples of the subject disclosure, in which like reference numerals represent similar parts throughout the several views of the drawings, and wherein:

FIGS. 5A and 5B collectively, is a flow chart illustrating a workflow for using the computer-based software application as configured by the workflow of FIGS. 1A, 1B and 1C to predict phase behavior of a live petroleum fluid sample.

DETAILED DESCRIPTION

Figure 1A:
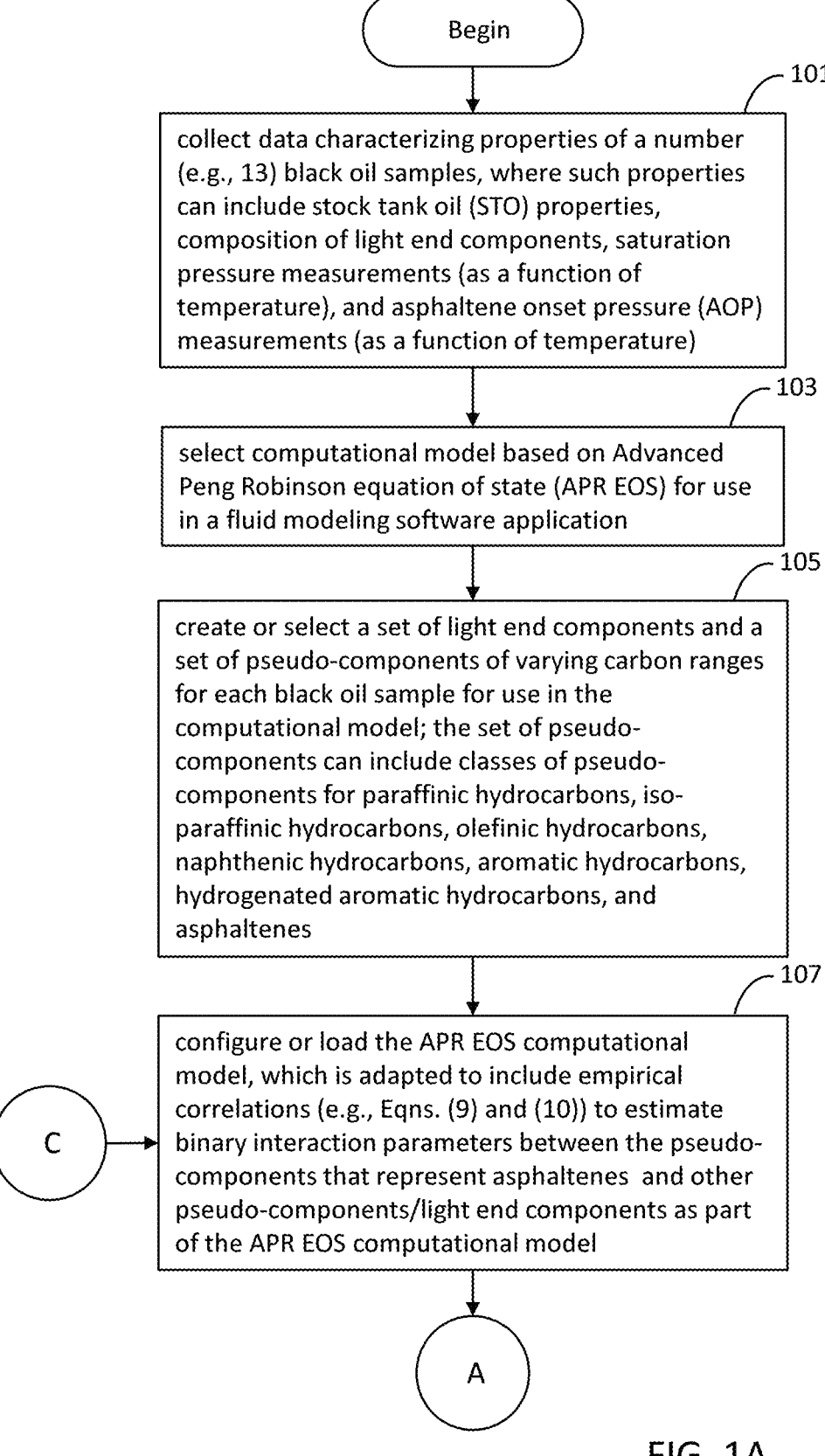
FIGS. 1A, 1B and 1C, collectively, are a flow chart illustrating a workflow for developing and configuring a computer-based fluid modeling software application that predicts phase behavior of petroleum fluids (e.g., crude oils)

The particulars shown herein are by way of example and for purposes of illustrative discussion of the embodiments of the subject disclosure only and are presented in the cause of providing what is believed to be the most useful and readily understood description of the principles and conceptual aspects of the subject disclosure. In this regard, no attempt is made to show structural details in more detail than is necessary for the fundamental understanding of the subject disclosure, the description taken with the drawings making apparent to those skilled in the art how the several forms of the subject disclosure may be embodied in practice. Furthermore, like reference numbers and designations in the various drawings indicate like elements.

The present disclosure provides for development and configuration of a fluid simulation software application and related computer-based methods and systems for modeling and predicting the phase behavior of petroleum fluids (e.g., crude oils) using a computational model based on an adaptation of the Advanced Peng Robinson equation of state (APR EOS). Such development was initiated by collecting meaningful experimental data from the literature where the data characterizes properties of a number of black oil samples (e.g., thirteen black oil samples). These black oil samples were obtained from different geographical locations with reported gas to oil ratio values ranging from 56 to 272 Sm3/m3. Then, the fluid simulation software application can be configured to characterize properties of each black oil sample through a PIONA characterization technique based on a molecular structure (paraffins, isoparaffins, olefins, naphthenes, aromatics or dehydrogenated aromatics, asphaltenes). A PIONA component slate can be created per black oil sample where the molecular groups are optimally distributed across the carbon number ranges so physical properties such as saturation pressure, bulk density of the stock-tank oil, and gas to oil ratio were accurately estimated. In embodiments, the PIONA component slate for each black oil sample represents maltenes (non-asphaltene hydrocarbons) by a set of light end components as well as a set of pseudo-components of varying carbon number and molecular structure for non-asphaltene hydrocarbons (e.g., paraffins, isoparaffins, olefins, naphthenes, aromatics, and aromatics dehydrogenated).

The fluid simulation software application can then be configured to employ a computational model based on adaptation of the APR EOS, which is referred to herein as APR EOS computational model, to characterize and model the phase equilibria of each black oil sample. In embodiments, the APR EOS computational model extends the PIONA component slate for each black oil sample to include a set of pseudo-components of varying carbon number for asphaltene hydrocarbons. The set of pseudo-components of varying carbon number for the asphaltene hydrocarbons can optionally include metals and heteroatoms, such as nitrogen (N), sulfur (S), vanadium (V), nickel (Ni), and iron (Fe). The PIONA component slate for each black oil sample can also include a set of pseudo-components of varying carbon number and molecular structure for asphaltene-like hydrocarbons (e.g., aromatics or dehydrogenated aromatics). This computational model introduces a set of binary interaction parameters that account for molecular interactions between dissimilar components or pseudo-components within a mixture.

In embodiments, the binary interaction parameters of the APR EOS computational model can include binary interaction parameters between the pseudo-components that represent asphaltenes and the pseudo-components that represent asphaltene-like hydrocarbons (e.g., aromatic and dehydrogenated aromatic hydrocarbons), binary interaction parameters between the pseudo-components that represent asphaltenes and the pseudo-components that represent the non-asphaltene hydrocarbons (e.g., paraffins, isoparaffins, olefins, and naphthenes), as well as binary interaction parameters between the pseudo-components for the asphaltenes. These binary interaction parameters are associated with respective pseudo-component pairs and are determined from a generalized set of correlations (e.g., empirical correlation functions) that involve certain properties or parameters associated with respective pseudo-component pairs as input variables. For example, the correlations can include: two carbon numbers for the two pseudo-components of each pseudo-component pair; two critical properties, such as critical volume, for the two pseudo-components of each pseudo-component pair; and a specific constant parameter value labeled Ak for each pseudo-component pair. In this case, the correlations are independent of fluid temperature.

Additionally or alternatively, the binary interaction parameters of the APR EOS computational model can include binary interaction parameters between the pseudo-components that represents asphaltenes and the light end components. These binary interaction parameters are associated with respective asphaltenic pseudo-component:light end component pairs and are determined from another generalized set of correlations (e.g., empirical correlation functions) that involve certain properties or parameters associated with respective asphaltenic pseudo-component:light end component pairs as input variables. For example, the correlations can include: two carbon numbers for the asphaltenic pseudo-component and the light end component of each pair; a specific constant parameter value labeled $A_k$ for each pair; and a temperature dependency. In this case, the correlations are dependent on fluid temperature.

In embodiments, the correlations each have a specific set of parameters (e.g., constant parameter value labeled Ak) that is tuned to best represent the bulk properties of the black oil samples to get a good initial estimate of the experimentally measured asphaltene onset pressures for the black oil samples. The final tuned values of the parameters (e.g., specific constant parameters Ak) can be used as input to the correlations to determine final values of the binary interaction parameters for the computational model. The final values of the binary interaction parameters can be stored in electronic form, for example as constants, and accessed for application in subsequent modeling where the asphaltene onset condition or other property of a new live oil sample needs to be determined. This process can eliminate the need of tuning the computational model, which is an outstanding improvement compared to the CPA and SAFT models. Instead, the molecular weight distribution of the asphaltenic fraction of the new live oil sample can be tuned from experimental measurements of the new live oil sample to study asphaltene onset conditions of the new live oil sample.

Finally, the fluid simulation software application can be configured to use the computational model (with tuned binary interaction parameters) to recharacterize properties of the asphaltenic fraction of each black oil sample to get a better match of the experimental asphaltene onset pressure measurements. In embodiments, this can be carried out by regressing the average molecular weight of the asphaltenic fraction of each black oil sample. For the number of black oil samples, the regressed average molecular weight of asphaltenes ranged from 2200 to 4200 g/mol.

Figure 1B:
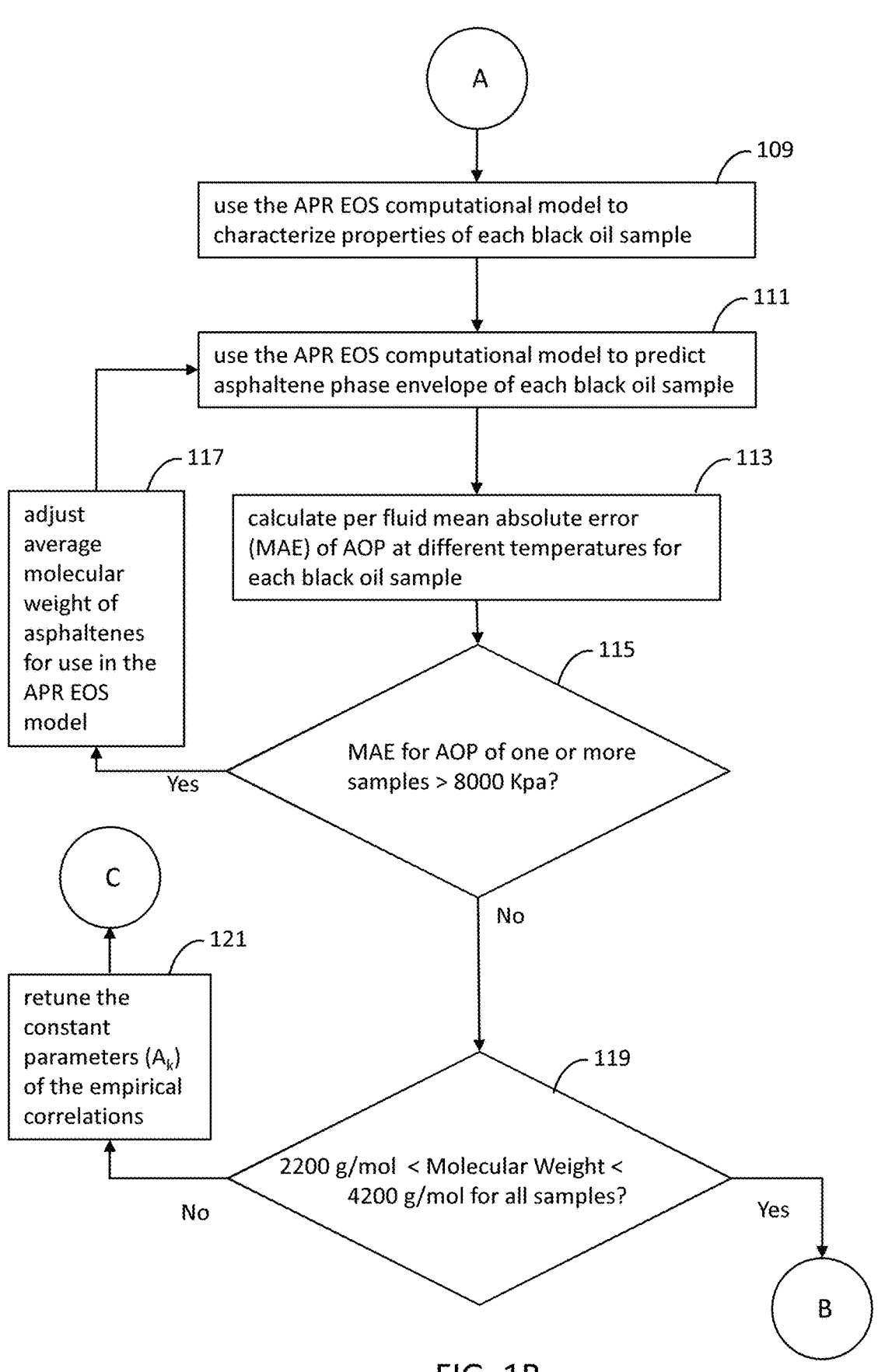
Figure 1C:
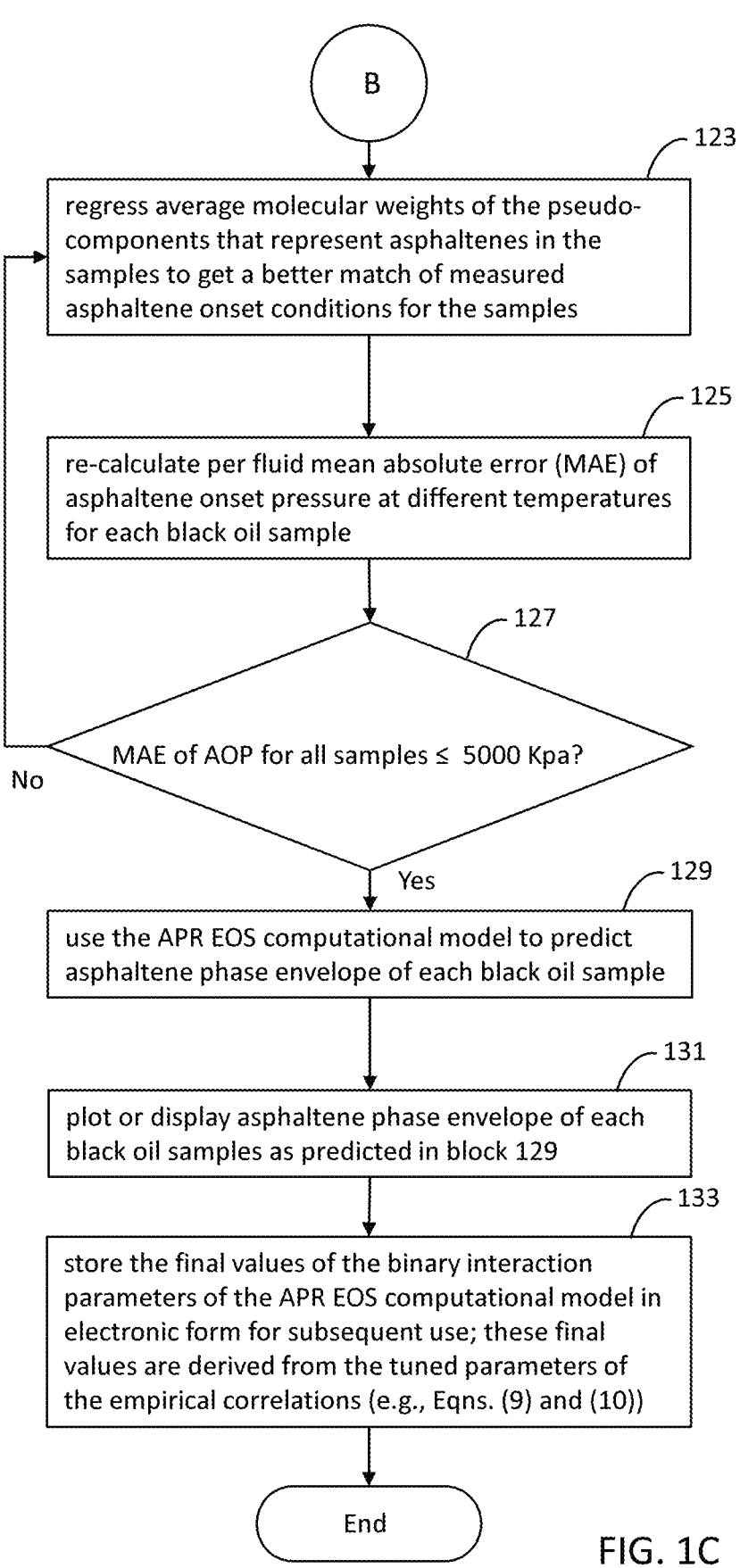

FIGS. 1A, 1B and 1C show a workflow used to develop and configure a fluid simulation software application and related computer-based methods and systems for modeling and predicting the phase behavior of petroleum fluids using an APR EOS computational model. In embodiments, the resulting fluid simulation software application and related computer-based methods and systems can be embodied in the Symmetry process software platform commercially available from Schlumberger.

In block 101, data is collected that characterizes properties of a number (e.g., 13) of black oil samples. In embodiments, such properties can include stock tank oil (STO) properties, composition of light end components, saturation pressure measurements (as a function of temperature), and asphaltene onset pressure (AOP) measurements (as a function of temperature).

In embodiments, the data for the black oil samples can be collected from the literature or other measurements, which for example can include the following set of analyses:

for the stock tank oil properties (residual liquid obtained after flashing the black oil sample at standard conditions): SARA mass composition and bulk density;

for the other properties: GC compositional analysis, Gas to Oil ratio, saturation pressure and asphaltene onset measurements at different temperatures.

In embodiments, the black oil samples can be made up of a variety of components including light ends, large, heavy, and non-volatile hydrocarbons.

In block 103, a computational model based on the APR EOS, which is referred to as APR EOS computational model, is selected for use in the fluid modeling software application to model and predict the phase behavior equilibria of the black oil samples. The selection of the APR EOS computational model can be performed manually by user input or by other means. In embodiments, the APR EOS computational model is defined by the following equation:

$$p = \frac{RT}{v-b} - \frac{a}{v^2 + 2vb - b^2}$$ Eqn. (1)

where p is the pressure, T is the absolute temperature, v is the molar volume and R is the gas constant; the parameters a and b describe the properties of the fluid; parameter a represents the tendency of the molecules to attract one another while parameter b defines the molecular size.

For a mixture, the average values of a and b can be determined from the Van der Waals mixing rules as follows:

$$a = \Sigma\Sigma(1 - k_{ij}) * \sqrt{a_i a_j} * x_i x_j \qquad \text{(Eq. 2)}$$

$$b = \Sigma x_i b_i \qquad \text{(Eq. 3)}$$

where $x_i x_j$ denote the mole fractions of components or pseudo-components i and j in the mixture. $k_{ij}$ are the binary interaction parameters, which are estimated based on empirical correlations.

For individual components or pseudo-components, the parameters $a_i$ and $b_i$ can be found by applying the following equations:

$$a_i = a_{ci} * \left(1 + f_{wi} * \left(1 - \sqrt{T/T_{ci}}\right)\right)^2 \qquad \text{(Eq. 4)}$$

$$a_{ci} = 0.457 \frac{R^2 * T_{ci}^2}{p_{ci}} \qquad \text{(Eq. 5)}$$

$$f_{wi} = 0.3746 + 1.542 w_i - 0.269 w_i^2 \text{ if } w_i < 0.52 \qquad \text{(Eq. 6)}$$

$$f_{wi} = 0.3796 + 1.485 w_i - 0.1644 w_i^2 + 0.0166 w_i^3 \text{ if } w_i > 0.52 \qquad \text{(Eq. 7)}$$

$$b_i = 0.07780 \frac{R * T_{ci}}{p_{ci}} \qquad \text{(Eq. 8)}$$

where $T_{ci}$ is the critical temperature, $p_{ci}$ is the critical pressure, and $w_i$ is the acentric factor.

In block 105, a set of light end components and a set of pseudo-components of varying carbon ranges are selected or created for each black oil sample for use in the APR EOS computational model. The selection or creation of the light end components and pseudo-components of the oil samples can be performed manually by user input or by other means. The set of pseudo-components can include classes of pseudo-components for paraffinic hydrocarbons, iso-paraffinic hydrocarbons, olefinic hydrocarbons, naphthenic hydrocarbons, aromatic hydrocarbons, dehydrogenated aromatic hydrocarbons, and asphaltenes.

Figure 2A:
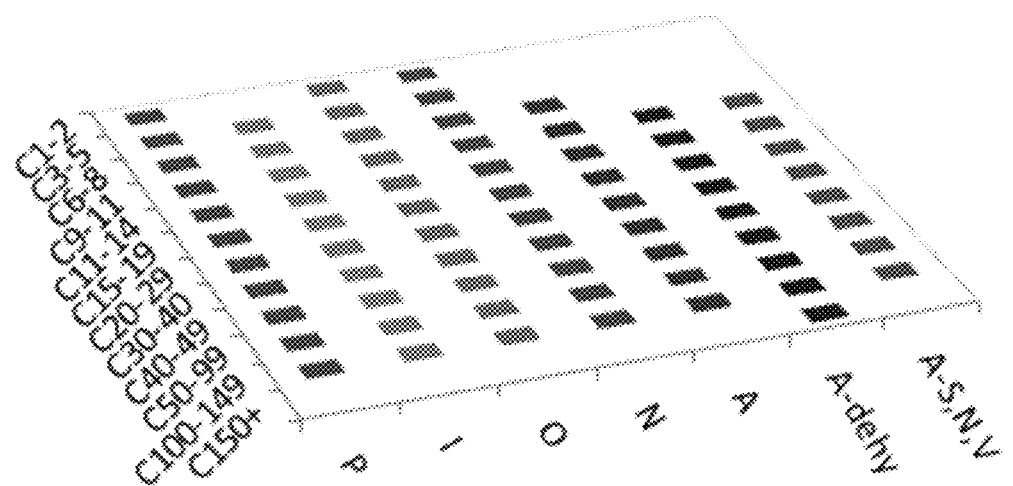
FIG. 2A is a schematic diagram illustrating an example PIONA pseudo-component slate for use in the computer-based fluid modeling software application configured by the workflow of FIGS. 1A, 1B and 1C.
Figure 2B:
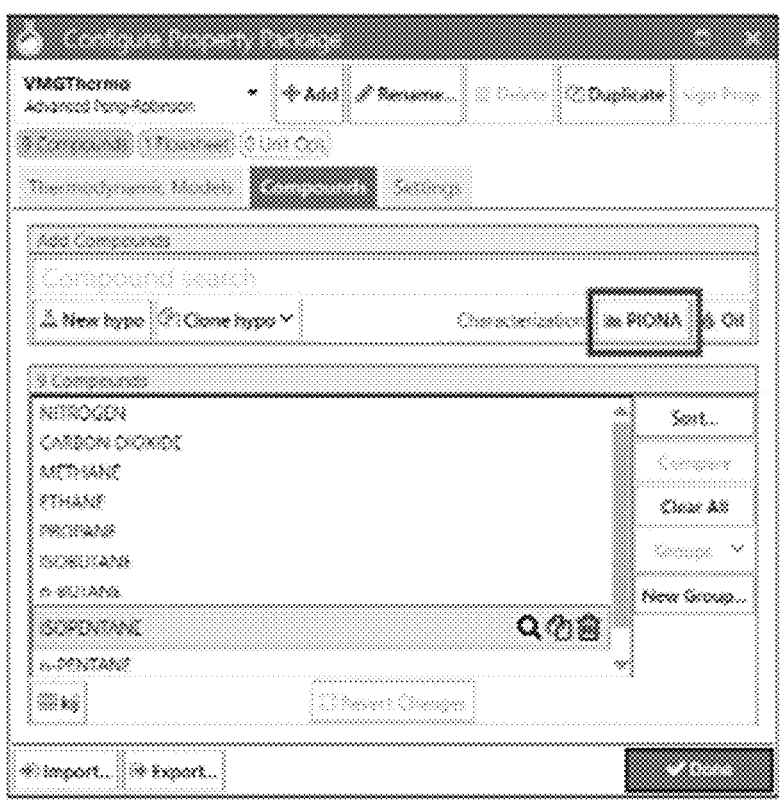
FIGS. 2B and 2C are display screens of graphical user interfaces that can be part of the computer-based fluid modeling software application configured by the workflow of FIGS. 1A, 1B and 1C.
Figure 2C:
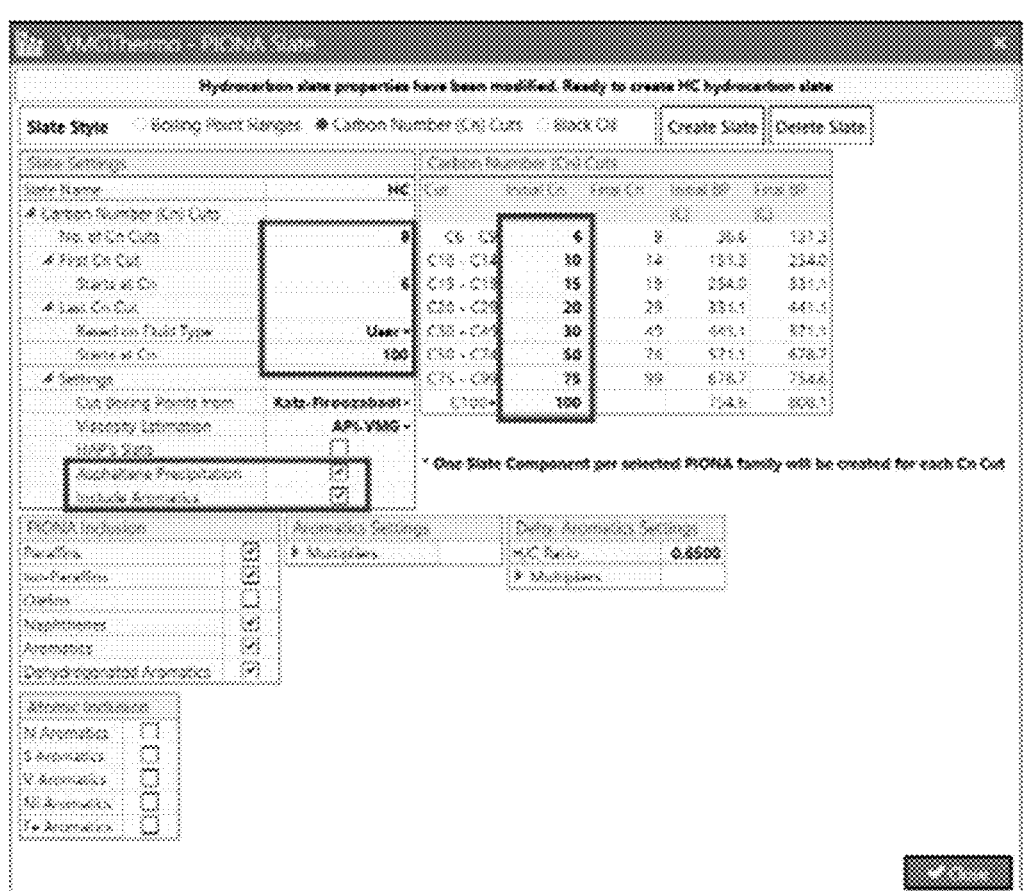

In embodiments, the pseudo-components for each black oil sample are defined by a consistent PIONA pseudo-component slate which is defined by two dimensions: the range of carbon numbers is based on the selected initial and end boiling points and the second dimension is determined by the type of PIONA chemical family as presented in the FIG. 2A. FIG. 2B illustrates a graphical user interface that enables a user to select one or more light end components for each black oil sample for use in the APR EOS computational model. FIG. 2C illustrates a graphical user interface that enables a user to define carbon number resolution and select one or more classes of pseudo-components for paraffinic hydrocarbons, iso-paraffinic hydrocarbons, olefinic hydrocarbons, naphthenic hydrocarbons, aromatic hydrocarbons, dehydrogenated aromatic hydrocarbons, and asphaltenes for each black oil sample for use in the APR EOS computational model.

In block 107, the APR EOS computational model can be configured to employ empirical correlations (e.g., Eqns. (9) and (10) below) that define the binary interaction parameters between the pseudo-components that represent asphaltenes and other pseudo-components/light end components as part of the APR EOS computational model.

In embodiments, the binary interaction parameter between a respective pseudo-component that represent asphaltenes (asp$_i$) and a respective pseudo-component that represent paraffins (para$_j$) can be calculated through the following expression which is a function of the carbon number, critical properties, and some specific constant values (A$_k$):

$$k_{asp_i - para_j} = f\left(A_k, Cn_{asp_i}, Cn_{para_j} V_{critical_{asp_i}}, V_{critical_{para_j}}\right) \qquad \text{(Eq. 9)}$$

where $Cn_{asp_i}$ and $Cn_{para_j}$ are the carbon numbers of the asphaltene pseudo-component i and the paraffin pseudo-component j, respectively. $V_{critical\_asp_i}$ and $V_{critical\_para_j}$ are the critical volumes of the asphaltene pseudo-component i and the paraffin pseudo-component j, respectively.

Similar expressions to the one presented in the Eqn. 9 can be applied to calculate the binary interaction parameter of other pairs of pseudo-components as follows:

Asphaltenes (i)—isoparaffins (j)
Asphaltenes (i)—naphthenes (j)
Asphaltenes (i)—aromatics (j)
Asphaltenes (i)—aromatics dehydrogenated (j)
Asphaltenes (i)—asphaltenes (j)

For each correlation between the asphaltene and each PIONA chemical family, the values of the constants A$_k$ can be tuned to get both a proper characterization of the saturation pressure curve for each black oil sample and a good initial estimate of the asphaltene onset pressure for each black oil sample.

For the light ends components (e.g., going from methane to pentane), a different empirical correlation can be used to calculate the binary interaction parameters as follows:

$$k_{asp_i-light\ ends} = f(A_k, Cn_{asp_i}, Cn_{para_j}, T) \qquad \text{(Eq. 10)}$$

Unlike the correlations of Eqn. 9, the expression given by the Eqn. 10 introduces dependency on fluid temperature (T) in the calculation of the binary interaction parameter for the asphaltene pseudo-component and the light end component pairs.

In block 109, the APR EOS computational model can be used to characterize properties of each black oil sample. For example, after setting the PIONA component slate and initial values of the binary interaction parameters using the correlations presented above, each black oil sample can be characterized by operation of the fluid modeling software application (e.g., oil source unit operation) by providing the minimum following input data:

Density and SARA composition of the stock tank oil
Composition of the light ends
Saturation pressure Once this information is specified, the APR EOS computational model can generate an initial characterization of each black oil sample based on five cuts with defined boiling point ranges. In embodiments, the APR EOS computational model can employ empirical correlations that calculate initial mass yield and density values for each cut. These empirical correlations are a function of the SARA composition, density of the stock tank oil, and content of the light end components.

Figure 3:
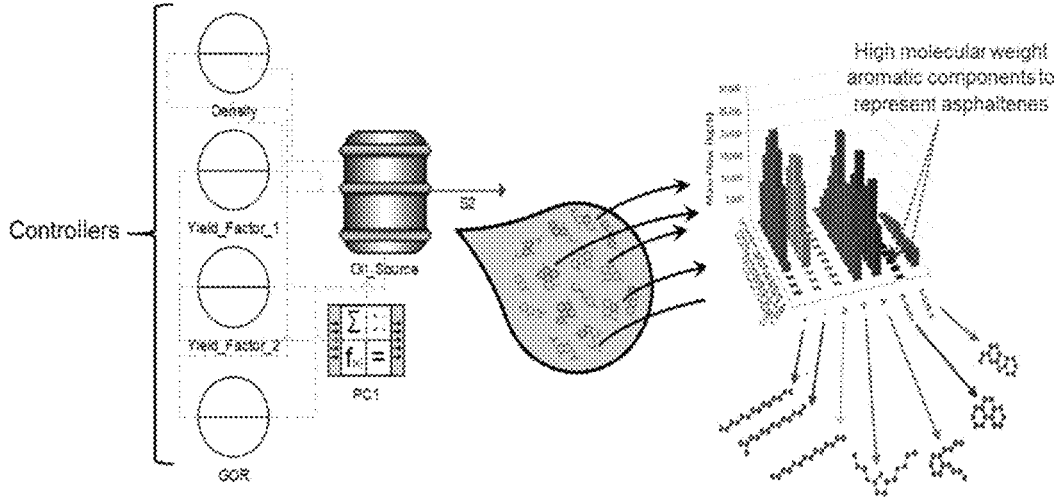
FIG. 3 is a schematic diagram illustrating example fluid characterization operations carried out by the computer-based fluid modeling software application as part of the workflow of FIGS. 1A, 1B and 1C.

Furthermore, the fluid modeling software application can be configured to match the bulk properties of the black oil samples. In embodiments, this matching operation can involve four distinct operations (e.g., controllers). The first operation matches bulk density of stock tank oil predicted by the APR EOS computational model to measured/experimental bulk density of the stock tank oil by adjusting a density factor. The second and third operations match the saturation pressure data predicted by the APR EOS computational model to measured/experimental saturation pressure data by adjusting two factors affecting the mass yield of the cut ranges. If a gas to oil ratio value is available, the fourth operation can provide an accurate estimation of this variable by adjusting the density of the lightest cut range. These four operations (e.g., controllers) can be iteratively solved until the error or difference between predicted and measured physical properties are minimized. The order of solving priority can be fixed for all four operations (e.g., controllers) to ensure a unique fluid characterization resulted. FIG. 3 shows a graphical representation of the characterization process carried out by operation of the fluid modeling software application.

In blocks 111 to 117, a procedure is carried out to tune the binary interaction parameters of the APR EOS computational model.

Figure 4A:
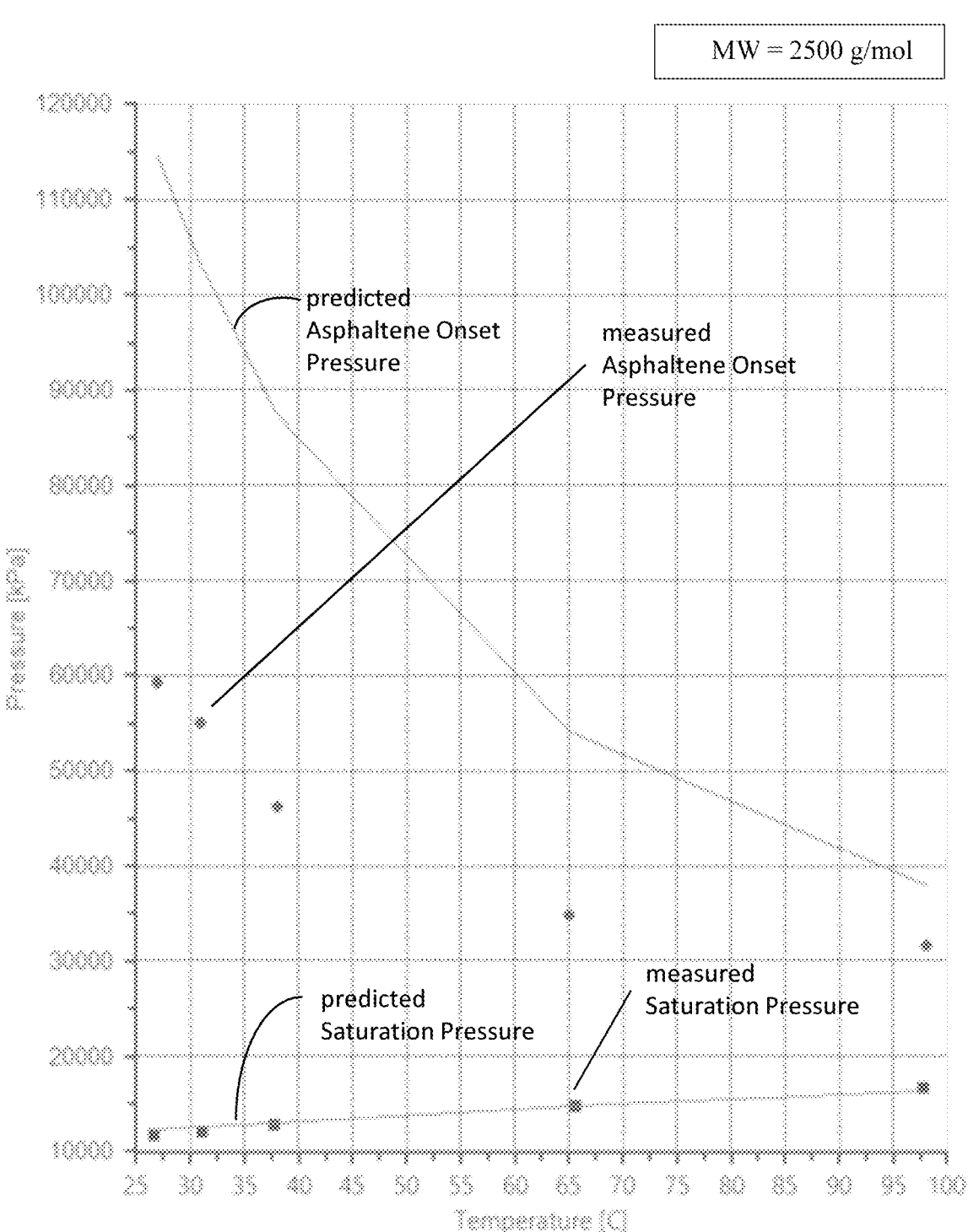
FIG. 4A is a plot or display of asphaltene phase envelope and saturation pressure data of a particular black oil sample (e.g., sample 3) predicted by the computational model of the computer-based fluid modeling software application configured by the workflow of FIGS. 1A, 1B and 1C, where the average molecular weight of asphaltenes is initially set to a default value of 2500 g/mol. It also shows experimental measurements of asphaltene phase envelope and saturation pressure data of the black oil sample (e.g., sample 3)

In the first iteration (block 111), the APR computational model can be used to predict asphaltene phase envelope of each black oil sample. For each black oil sample, this phase diagram shows the conditions of pressure and temperature at which the asphaltenes start dropping out above a set minimum mole fraction tolerance and the saturation pressure line as illustrated in FIG. 4A.

In block 113, a per sample mean absolute error (MAE) of asphaltene onset pressure (AOP) can be calculated based on the difference between the asphaltene onset pressure predicted (or calculated) by the APR EOS computational model and the experimental measured asphaltene onset pressure at different temperatures for each black oil sample. In embodiments, the mean absolute error of the asphaltene onset pressure (MAE AOP) can be calculated for a given black oil sample using the following equation:

$$MAE\ AOP = \frac{\sum_k^n \left(AOP^i_{calc} - AOP^i_{exp}\right)}{n} \qquad \text{Eqn. (11)}$$

where n is the total number of data points, $$AOP^i_{calculated}\ \text{and}\ AOP^i_{exp}$$

are the predicted (or calculated) and the experimental asphaltene onset pressures at a temperature i, respectively.

In block 115, operations can check whether the mean absolute error of the asphaltene onset pressure (MAE AOP) of one or more samples is greater than 8000 Kpa. If so, the operations continue to 117. If not, the operations continue to 119.

In block 117, operations can adjust average molecular weight of asphaltenes in the APR EOS computational model for those samples having MAE AOP higher than 8000 KPa. Once the errors of all samples were brought down below 8000 KPa (first criteria), the operations continue to block 119.

In block 119, the operations can check whether the molecular weight (MW) of all the samples falls within the range of 2200 to 4200 g/mol (second criteria). If this second condition is not met, the operations continue to block 121 where the constant values $(A_k)$ of the empirical correlations developed for estimating the binary interaction parameters of the APR EOS computational model are adjusted or retuned, and the operations return to block 107 to repeat the operations of blocks 107 to 119. If this second condition is met, the operations continue to blocks 123 to 127.

In blocks 123 to 127, the molecular weights of the pseudo-components that represent asphaltenes in the samples can be adjusted to get a better match of measured asphaltene onset conditions for the black oil samples. In embodiments, this can involve predicting new asphaltene onset pressures at different temperatures for each black oil sample (block 123), predicting or calculating corresponding mean absolute error (using the APR EOS computational model) relative to the measured asphaltene onset conditions for the black oil samples (block 125) and checking whether the MAE AOP for all samples is less than or equal to 5000 Kpa (block 127). If the criteria is not satisfied for all samples (2200<MW<4200), the molecular weights of the pseudo-components that represent asphaltenes in the black oil samples can be adjusted and the procedure of blocks 123 to 127 repeated. If the criteria is satisfied, the operations can continue to block 129.

In embodiments, the operations of blocks 123 to 127 can be configured to recharacterize the asphaltenic fraction of the black oil samples in order to get a better match of the asphaltene onset pressure data. Such recharacterization can make a rigorous adjustment of the molecular weight distribution of asphaltenes.

In embodiments, the following gamma distribution can be used to represent the molecular weight distribution of asphaltenes:

$$f(MW) = \frac{(MW - MW_{mono})^{\alpha-1}}{\beta^\alpha \Gamma(\alpha)} \exp\left(\frac{MW_{mono} - MW}{\beta}\right) \qquad \text{Eqn. (11)}$$

$$\beta = \frac{MW_{avg} - MW_{mono}}{\alpha} \qquad \text{Eqn. (12)}$$

where $MW_{mono}$ is the monomer molecular weight, a is the shape factor of the distribution, and $MW_{avg}$ is the average molecular weight.

The last parameter $MW_{avg}$ can be tuned to get a closer match between predicted asphaltene onset pressure (calculated using the APR EOS) and the experimental asphaltene onset pressure while the monomer molecular weight and the shape factor were set to constant values of 1000 g/mol and 3, respectively. The regression procedure can be repeated until the mean absolute error of all black oil samples is lower than about 5000 KPa.

In block 129, the resulting APR EOS computational model (e.g., with tuned binary interaction parameters and tuned molecular weights of the pseudo-components that represent asphaltene) can be used to predict the asphaltene phase envelope of each black oil sample.

In block 131, the asphaltene phase envelope of each black oil samples as predicted in block 129 can be plotted or displayed.

In block 133, the final values of the binary interaction parameters of the APR EOS computational model can be stored in electronic form for subsequent use. These final values are derived from the tuned parameters of the empirical correlations (e.g., Eqns. (9) and (10)). These final values can be stored as part of the APR EOS computational model of the fluid modeling software application that models and predict phase behavior of petroleum fluids.

Working Example

This working example was carried out using the data of a particular crude oil sample (labeled "fluid 3") with a GOR value of 100.6 Sm3/m3. The data was reported by Gonzalez et al., 2012. See Gonzalez, D. L., Mahmoodaghdam, E., Lim, F., Joshi, N. Effects of Gas Additions to Deepwater Gulf of Mexico Reservoir Oil: Experimental Investigation of Asphaltene Precipitation and Deposition. Society of Petroleum Engineers (SPE) 159098, 2012.

Then, a PIONA component slate was created in a fluid modeling software application (e.g., Symmetry) that models and predict phase behavior of petroleum fluids. In embodiments, the PIONA component slate includes ten (10) pure pseudo-components and ninety-three (93) PIONA pseudo-components. An APR EOS computational model was selected. This APR EOS computational model was configured to include the generalized set of correlations that were developed to calculate the binary interaction parameters of the model. The final values of the binary interactions parameters was tuned according to the workflow of FIGS. 1A, 1B and 1C and stored (e.g., hard coded) within the fluid modeling software application.

Later, data representing properties of the particular crude oil sample (labeled "fluid 3") was entered as input to the fluid modeling software application, and the fluid modeling software application was configured to match the bulk properties of the oil samples. In embodiments, this matching operation can involve four distinct operations (e.g., controllers). The first operation matches the bulk density of stock tank oil predicted by the APR EOS to the measured/experimental bulk density of the stock tank oil by adjusting a density factor. The second and third operations match saturation pressure data predicted by the APR EOS to measured/experimental saturation pressure data by adjusting two factors affecting the mass yield of the cut ranges. If a gas to oil ratio value is available, the fourth operation can provide an accurate estimation of this variable by adjusting the density of the lightest cut range. These four operations (e.g., controllers) can be iteratively solved until the error between predicted and measured physical properties are minimized. The order of solving priority can be fixed for all four operations (e.g., controllers) to ensure a unique fluid characterization resulted. FIG. 3 shows a graphical representation of this characterization process. Once these four operations were activated and solved, the fluid modeling software application estimated the final saturation pressure, density of the stock tank oil and gas to oil ratio with relative errors of 2.9%, 3.4% and 5.6% respectively.

Later, the fluid modeling software application (with the APR EOS computational model as described herein) was used to predict the asphaltene onset pressures at five different temperatures for the particular crude oil sample (labeled "fluid 3") as illustrated in FIG. 4A. Note that the continuous line labeled "predicted Asphaltene Onset Pressure" in FIG. 4A is the asphaltene onset pressure predicted by the APR EOS computational model, while the circles are the corresponding measured/experimental data of the asphaltene onset pressure for the particular crude oil sample (labeled "fluid 3"). Furthermore, the continuous line labeled "predicted Saturation Pressure" in FIG. 4A corresponds to the saturation pressure predicted by the APR EOS computational model, and the squares are the corresponding measured/experimental data of the saturation pressure for the particular crude oil sample (labeled "fluid 3"). FIG. 4A shows that the predicted values of the asphaltene onset pressure did not accurately match the experimental data using a default value for the average molecular weight equal to 2500 g/mol.

Figure 4B:
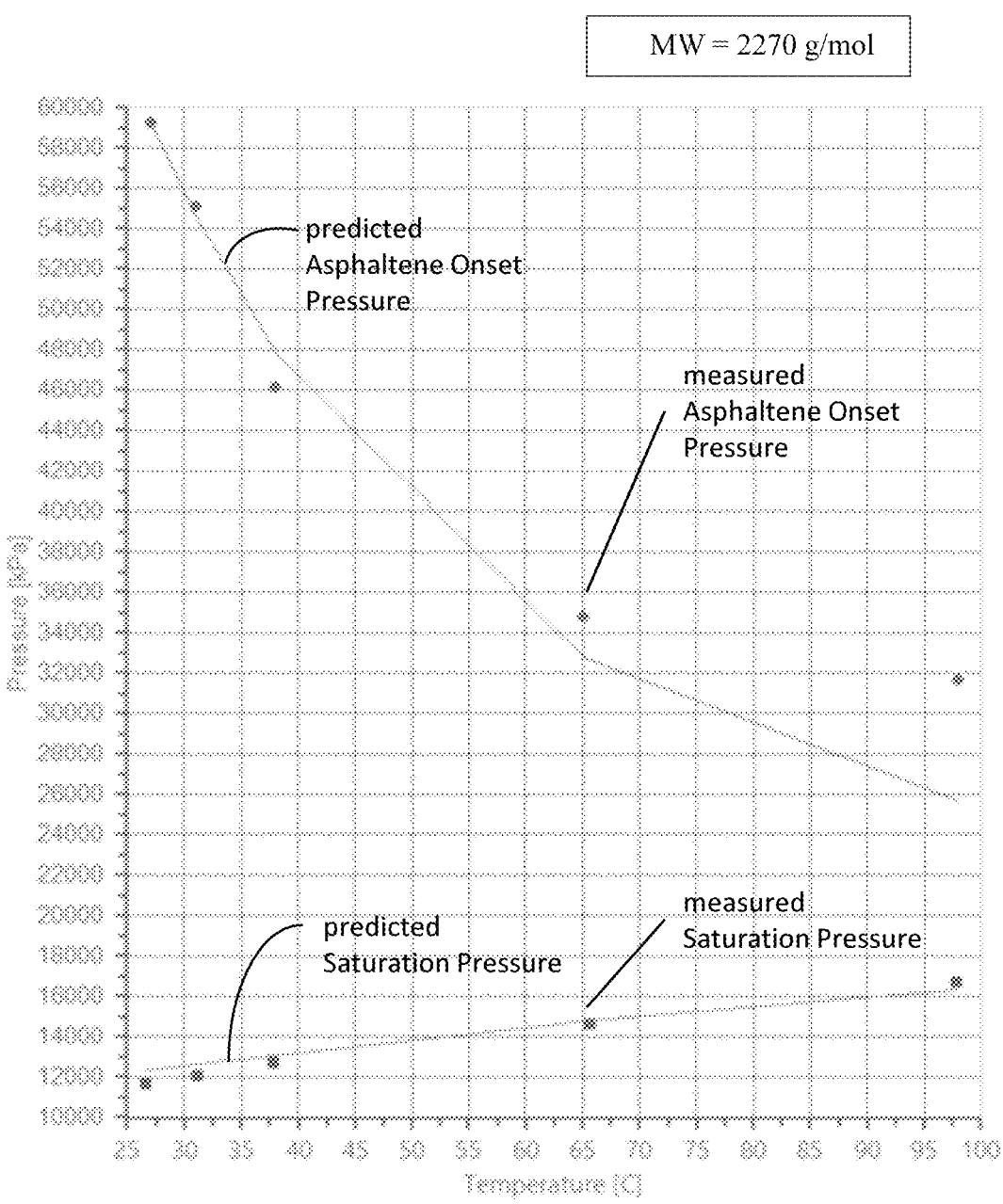
FIG. 4B is a plot or display of asphaltene phase envelope and saturation pressure data of a particular black oil sample (e.g., sample 3) predicted by the computational model of the computer-based fluid modeling software application configured by the workflow of FIGS. 1A, 1B and 1C, where the average molecular weight of asphaltenes was adjusted to a value of 2270 g/mol. It also shows experimental measurements of asphaltene phase envelope and saturation pressure data of the black oil sample (e.g., sample 3)

In order to minimize the error and improve the accuracy of these predictions, the molecular weight distribution of asphaltenes in the particular crude oil sample (labeled "fluid 3") was adjusted such that the average molecular weight was 2270 g/mol, and the fluid modeling software application (with computational model as described above) was used to predict the asphaltene onset pressures at five different temperatures for the particular crude oil sample (labeled "fluid 3") as illustrated in FIG. 4B. These predictions were more accurate and provide a final mean absolute error of 2060 KPa, which is lower than 5000 KPa.

Figure 5B:
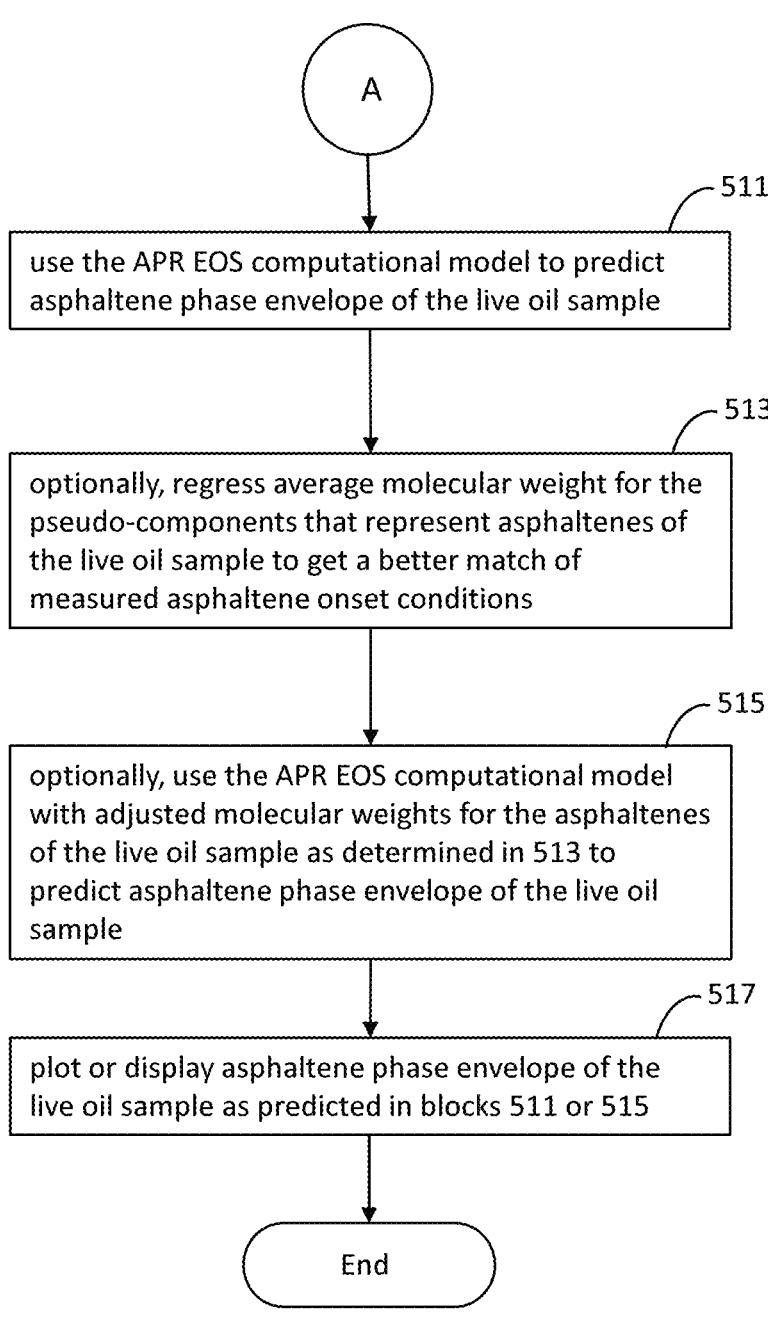

FIGS. 5A and 5B, collectively, is a flowchart that shows a workflow that uses the fluid simulation software application and related computer-based methods and systems for modeling and predicting the phase behavior of petroleum fluids using an APR EOS computational model as developed and configured as described above with respect to FIGS. 1A, 1B and 1C.

In block 501, data is collected that characterizes properties of a live oil sample (e.g., petroleum fluid of interest). In embodiments, such properties can include stock tank oil (STO) properties, composition of light end component, and possibly other properties.

In block 503, an APR EOS computational model as described herein can be selected for use in the fluid modeling software application. The selection of the computational model can be performed manually by user input or by other means.

In block 505, a set of light end components and a set of pseudo-components of varying carbon ranges for the live oil sample can be selected for use in the APR EOS model. The selection of the light end components and pseudo-components of the live oil sample can be performed manually by user input or by other means. The set of pseudo-components can include classes of pseudo-components for paraffinic hydrocarbons, iso-paraffinic hydrocarbons, olefinic hydrocarbons, naphthenic hydrocarbons, aromatic hydrocarbons, hydrogenated aromatic hydrocarbons, and asphaltenes. The set of light end components and the set of pseudo-components can match the components and pseudo-components of the computational model used in the workflow of FIGS. 1A, 1B and 1C. FIG. 2B illustrates a graphical user interface that enables a user to select one or more light end components for each black oil sample for use in the APR EOS computational model. FIG. 2C illustrates a graphical user interface that enables a user to define the carbon number resolution and to select one or more classes of pseudo-components for paraffinic hydrocarbons, iso-paraffinic hydrocarbons, olefinic hydrocarbons, naphthenic hydrocarbons, aromatic hydrocarbons, dehydrogenated aromatic hydrocarbons, and asphaltenes for each black oil sample for use in the APR EOS computational model.

In block 507, the APR EOS computational model can be configured to use the binary interaction parameters stored in block 133 for modeling the live oil sample.

In block 509, the APR EOS computational model (which is configured with the binary interaction parameters stored in block 133) is used to characterize properties of the live oil sample.

In block 511, the APR EOS computational model (which is configured with the binary interaction parameters stored in block 133) is used to predict asphaltene phase envelope of the live oil sample.

In optional block 513, the average molecular weight for the pseudo-components that represent asphaltenes of the live oil sample can be adjusted or regressed to get a better match of measured asphaltene onset conditions of the live oil sample. These operations are similar to those described above with respect to blocks 123 to 127 of the flowchart of FIGS. 1A, 1B and 1C.

In optional block 515, the APR EOS computational model (which is configured with the binary interaction parameters stored in block 133) can be used with the updates for the molecular weight for the pseudo-components that represent asphaltenes of the live oil sample as determined in 513 to predict asphaltene phase envelope of the live oil sample.

In block 517, the asphaltene phase envelope of the live oil sample as predicted in block 511 or block 515 can be plotted or displayed. The plot or display of the resulting asphaltene phase envelope can be similar to the plots shown in FIGS. 4A and 4B.

Figure 6:
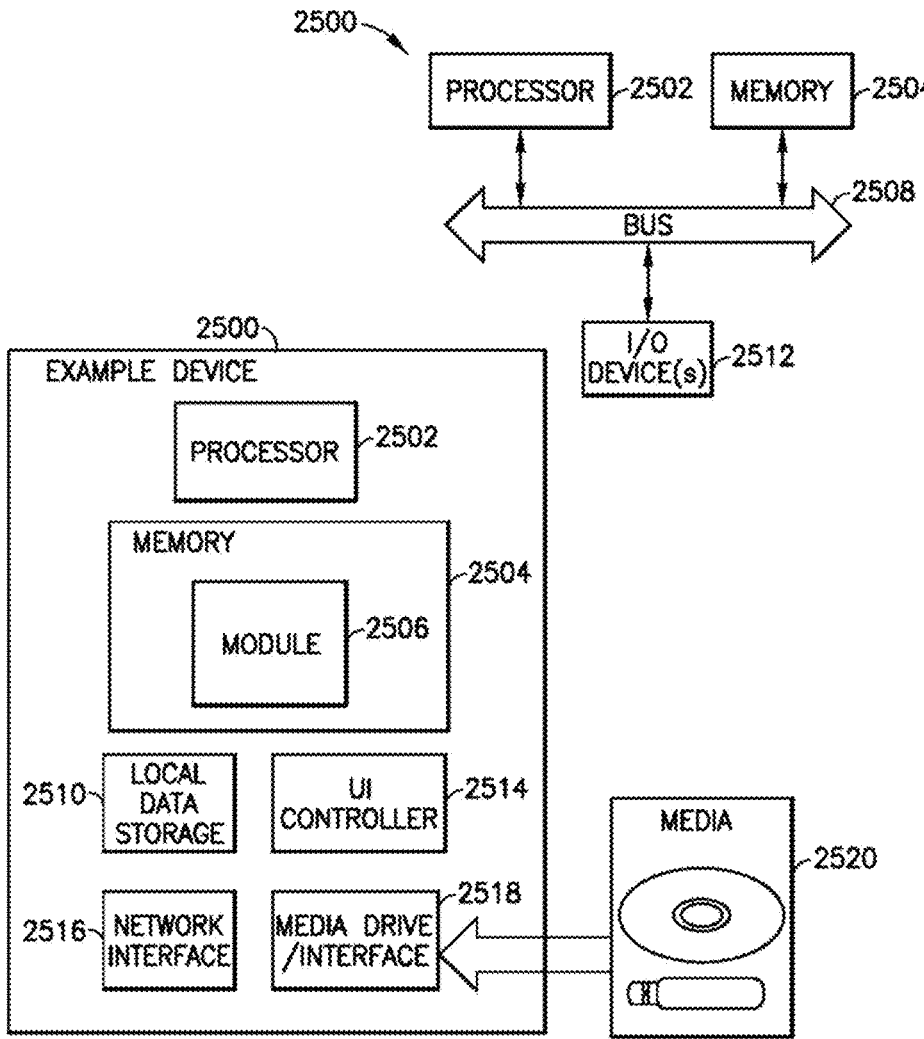
FIG. 6 is a block diagram of a computer processing system.

FIG. 6 illustrates an example device 2500, with a processor 2502 and memory 2504 that can be configured to implement various embodiments of the computer-based methods and systems that model and predict phase behavior of petroleum fluids or crude oils as discussed in this disclosure. Memory 2504 can also host one or more databases and can include one or more forms of volatile data storage media such as random-access memory (RAM), and/or one or more forms of nonvolatile storage media (such as read-only memory (ROM), flash memory, and so forth).

Device 2500 is one example of a computing device or programmable device and is not intended to suggest any limitation as to scope of use or functionality of device 2500 and/or its possible architectures. For example, device 2500 can comprise one or more computing devices, programmable logic controllers (PLCs), etc.

Further, device 2500 should not be interpreted as having any dependency relating to one or a combination of components illustrated in device 2500. For example, device 2500 may include one or more of computers, such as a laptop computer, a desktop computer, a mainframe computer, etc., or any combination or accumulation thereof.

Device 2500 can also include a bus 2508 configured to allow various components and devices, such as processors 2502, memory 2504, and local data storage 2510, among other components, to communicate with each other.

Bus 2508 can include one or more of any of several types of bus structures, including a memory bus or memory controller, a peripheral bus, an accelerated graphics port, and a processor or local bus using any of a variety of bus architectures. Bus 2508 can also include wired and/or wireless buses.

Local data storage 2510 can include fixed media (e.g., RAM, ROM, a fixed hard drive, etc.) as well as removable media (e.g., a flash memory drive, a removable hard drive, optical disks, magnetic disks, and so forth).

One or more input/output (I/O) device(s) 2512 may also communicate via a user interface (UI) controller 2514, which may connect with I/O device(s) 2512 either directly or through bus 2508.

In one possible implementation, a network interface 2516 may communicate outside of device 2500 via a connected network.

A media drive/interface 2518 can accept removable tangible media 2520, such as flash drives, optical disks, removable hard drives, software products, etc. In one possible implementation, logic, computing instructions, and/or software programs comprising elements of module 2506 may reside on removable media 2520 readable by media drive/interface 2518.

In one possible embodiment, input/output device(s) 2512 can allow a user (such as a human annotator) to enter commands and information to device 2500, and also allow information to be presented to the user and/or other components or devices. Examples of input device(s) 2512 include, for example, sensors, a keyboard, a cursor control device (e.g., a mouse), a microphone, a scanner, and any other input devices known in the art. Examples of output devices include a display device (e.g., a monitor or projector), speakers, a printer, a network card, and so on.

Various systems and processes and workflows of present disclosure may be described herein in the general context of software or program modules, or the techniques and modules may be implemented in pure computing hardware. Software generally includes routines, programs, objects, components, data structures, and so forth that perform particular tasks or implement particular abstract data types. An implementation of these modules and techniques may be stored on or transmitted across some form of tangible computer-readable media. Computer-readable media can be any available data storage medium or media that is tangible and can be accessed by a computing device. Computer readable media may thus comprise computer storage media. "Computer storage media" designates tangible media, and includes volatile and non-volatile, removable and non-removable tangible media implemented for storage of information such as computer readable instructions, data structures, program modules, or other data. Computer storage media include, but are not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other tangible medium which can be used to store the desired information, and which can be accessed by a computer. Some of the methods and processes described above, can be performed by a processor. The term "processor" should not be construed to limit the embodiments disclosed herein to any particular device type or system. The processor may include a computer system. The computer system may also include a computer processor (e.g., a microprocessor, microcontroller, digital signal processor, general-purpose computer, special-purpose machine, virtual machine, software container, or appliance) for executing any of the methods and processes described above.

The computer system may further include a memory such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device.

Some of the methods and processes and workflows described above, can be implemented as computer program logic for use with the computer processor. The computer program logic may be embodied in various forms, including a source code form or a computer executable form. Source code may include a series of computer program instructions in a variety of programming languages (e.g., an object code, an assembly language, or a high-level language such as C, C++, or JAVA). Such computer instructions can be stored in a non-transitory computer readable medium (e.g., memory) and executed by the computer processor. The computer instructions may be distributed in any form as a removable storage medium with accompanying printed or electronic documentation (e.g., shrink wrapped software), preloaded with a computer system (e.g., on system ROM or fixed disk), or distributed from a server or electronic bulletin board over a communication system (e.g., the Internet or World Wide Web).

Alternatively or additionally, the processor may include discrete electronic components coupled to a printed circuit board, integrated circuitry (e.g., Application Specific Integrated Circuits (ASIC)), and/or programmable logic devices (e.g., a Field Programmable Gate Arrays (FPGA)). Any of the methods and processes described above can be implemented using such logic devices.

Advantages/Potential Uses

The parameters of the prior art CPA and SAFT thermodynamic computational models must be tuned for each type of fluid, while the approach through the adaption of the APR EOS eliminates the need of tuning any parameter of this equation of state. Furthermore, the correlations for estimating the binary interaction parameters as described herein can be universally applied to any type of live oil sample since they are a function of the carbon number and the PIONA chemical family.

Moreover, the prior art CPA and SAFT thermodynamic computational models have extra tuning parameters apart from the binary interaction parameters which makes the tuning procedure more complicated. For instance, the CPA model (Arya et al., 2015) introduces four (4) new parameters which are the self-association energy ($\varepsilon^{AA}/R$) and self-association volume ($\beta^{AA}$) between asphaltene molecules, cross association energy ($\varepsilon^{AB}/R$) and cross association volume ($\beta^{AB}$) between asphaltene molecules and heavy hydrocarbon components. See Arya, A., von Solms, N., Kontogeorgis, G. M. Determination of asphaltene onset conditions using the cubic plus association equation of state. Fluid Phase Equilibria 400, 2015, 8-19.

Similarly, the SAFT model (Panaganti et al., 2013) has three extra parameters that are required to be estimated for each pseudo-component representing the fluid: number of segments per molecule (m), the temperature-independent diameter of each molecular segment ($\sigma$), and the segment-segment dispersion energy ($\varepsilon$). See Panuganti, S. R., Tavakkoli, M., Vargas, F. M., Gonzalez, D. L., Chapman, W. G. SAFT model for upstream asphaltene applications. Fluid Phase Equilibria 359, 2013, 2-16.

The total number of tuning parameters of the prior art CPA and SAFT model will depend on the characterization resolution of the sample; the higher the resolution, the more complicated the tuning of these thermodynamic models.

The computational model based on adaption of the Advanced Peng Robinson equation of state as described herein offers a more simplified approach to model the precipitation of asphaltenes of live oil samples since the Advanced Peng Robinson equation of state does not require further tuning for new fluids. If tuning is necessary, the average molecular weight of asphaltenes in the fluid itself can be adjusted to match measured asphaltene onset pressure data.

The computational model based on adaption of the Advanced Peng Robinson equation of state as described herein can be used at any characterization resolution selected to represent the fluid due to the calculation of the binary interaction parameters being based on the carbon number and the PIONA chemical family.

Furthermore, the suggested workflow for modeling the precipitation of asphaltenes can be applied to any type of characterization resolution selected for the reservoir fluid under investigation.

For example, any numbers of different fluids can be characterized and blended without the need of introducing additional pseudo-components. Such analysis can be used to study asphaltene stability of blends, and the effect of the blending order. Blending becoming naturally seamless between multiple fluids, due to the consistent PIONA component basis.

In another example, the effect of injecting inhibitors into the reservoir on the onset of the asphaltene precipitation can be studied. In this situation, special tuning of interaction parameters between the inhibitor and asphaltene components to match available data would be required.

In yet another example, for enhanced oil recovery methods, the computational model based on adaption of the Advanced Peng Robinson equation of state as described herein can be employed to study the asphaltene stability of live oils after injecting gas to the reservoir.

In still another example, the computational model based on adaption of the Advanced Peng Robinson equation of state as described herein can be employed to study asphaltene phase envelopes of live oils when the asphaltene concentration changes with formation depth.

Although only a few examples have been described in detail above, those skilled in the art will readily appreciate that many modifications are possible in the examples without materially departing from this subject disclosure. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112, paragraph 6 for any limitations of any of the claims herein, except for those in which the claim expressly uses the words 'means for' together with an associated function.

What is claimed is:

1. A method for predicting phase behavior of petroleum fluids, the method comprising:

configuring a computational model for predicting phase behavior equilibria of a first petroleum fluid sample, the computational model including pseudo-components representing fractions of the first petroleum fluid sample and binary interaction parameters associated with the pseudo-components, the pseudo-components including a set of pseudo-components representing asphaltenes, the binary interaction parameters including a set of at least two binary interaction parameters that are associated with the pseudo-components representing asphaltenes and that are defined by correlations each involving a plurality of adjustable parameters as input;

obtaining a measured fluid property for the first petroleum fluid sample;

determining values for the set of binary interaction parameters that are associated with the pseudo-components representing asphaltenes of the first petroleum fluid sample by tuning each of the plurality of adjustable parameters of the correlations, including two factors affecting mass yield, based on the measured fluid property for the first petroleum fluid sample, the tuning comprising adjusting each of the plurality of adjustable parameters for one or more of the correlations until a plurality of predefined matching criteria is satisfied, the plurality of predefined matching criteria including at least a first matching criterion and a second matching criterion, the second matching criterion being based on molecular weights for asphaltenes for a plurality of different petroleum fluid samples falling within a predefined range of molecular weight of from 2200 g/mol to 4200 g/mol, such that molecular weights for asphaltenes for all of the different petroleum fluid samples fall within the predefined range of molecular weight of from 2200 g/mol to 4200 g/mol;

after tuning each of the plurality of adjustable parameters of the correlations based on the measured fluid property for the first petroleum fluid sample, using the computational model to predict and display asphaltene phase onset as a function of temperature for the first petroleum fluid sample;

storing in electronic form the values for the set of binary interaction parameters that are associated with the pseudo-components representing asphaltenes for subsequent use as part of the computational model;

obtaining a measured fluid property for a second petroleum fluid sample; and using the computational model, including the stored values for the set of binary interaction parameters that are associated with the pseudo-components representing asphaltenes, to predict and display asphaltene phase onset as a function of temperature for the second petroleum fluid sample.

2. The method of claim 1, wherein the tuning involves matching the measured fluid property for the first petroleum fluid sample to a corresponding fluid property predicted by the computational model.

3. The method of claim 2, wherein the tuning involves adjusting each of the plurality of adjustable parameters for one or more correlations until error or difference between the measured fluid property for the first petroleum fluid sample and the corresponding fluid property predicted by the computational model satisfies at least one of the plurality of predefined matching criteria.

4. The method of claim 1, wherein the measured fluid property for the first petroleum fluid sample is based on measurements of asphaltene onset pressure for the first petroleum fluid sample.

5. The method of claim 1, wherein the tuning involves adjusting each of the plurality of adjustable parameters for one or more of the correlations based on matching at least one bulk fluid property measured for a plurality of different petroleum fluid samples and corresponding at least one bulk fluid property predicted by the computational model for the plurality of different petroleum fluid samples.

6. The method of claim 1, wherein the first matching criterion is based on error or difference between measurements of asphaltene onset pressure for the plurality of different petroleum fluid samples and corresponding asphaltene onset pressure predicted by the computational model for the plurality of different petroleum fluid samples.

7. The method of claim 6, wherein the error or difference error comprises a mean error of asphaltene onset pressure.

8. The method of claim 1, further comprising, after tuning the plurality of adjustable parameters of the correlations based on the measured fluid property for the first petroleum fluid sample, adjusting molecular weights for the pseudo-components representing asphaltenes of the first petroleum fluid sample until at least one additional matching criterion is satisfied.

9. The method of claim 8, wherein the at least one additional matching criterion is based on error or difference between measurements of asphaltene onset pressure for a plurality of different petroleum fluid samples and corresponding asphaltene onset pressure predicted by the computational model for the plurality of different petroleum fluid samples.

10. The method of claim 9, wherein the error or difference error comprises a mean error of asphaltene onset pressure.

11. The method of claim 1, wherein the computational model is based on an Advanced Peng Robinson equation of state.

12. The method of claim 1, wherein the binary interaction parameters of the computational model include at least one of:

i) binary interaction parameters between pseudo-components that represent asphaltenes and pseudo-components that represent asphaltene-like hydrocarbons;

ii) binary interaction parameters between pseudo-components that represent asphaltenes and pseudo-components that represent non-asphaltene hydrocarbons; or iii) binary interaction parameters between pseudo-components that represent asphaltenes.

13. The method of claim 1, wherein the correlations associated with the pseudo-components that represent asphaltenes involve certain properties or parameters associated with respective pseudo-component pairs as input variables.

14. The method of claim 13, wherein the correlations include at least one of:

i) two carbon numbers for the two pseudo-components of a respective pseudo-component pair;

ii) two critical properties for the two pseudo-components of the respective pseudo-component pair; or iii) a specific constant parameter value for the respective pseudo-component pair, the constant parameter value comprising the plurality of adjustable parameters that are subject to the tuning.

15. The method of claim 14, wherein the correlations are independent of fluid temperature.

16. The method of claim 1, wherein the binary interaction parameters of the computational model include at least binary interaction parameters between the pseudo-components that represents asphaltenes and light end components.

17. The method of claim 16, wherein the correlations involve certain properties or parameters associated with respective asphaltenic pseudo-component and light end component pairs as input variables.

18. The method of claim 17, wherein the correlations include at least one of:

i) two carbon numbers for the asphaltenic pseudo-component and the light end component of a respective pair;

ii) a specific constant parameter value Ak for the respective pair; or iii) a temperature value such that the correlations are dependent on fluid temperature.

19. The method of claim 17, wherein the computational model is part of a fluid modeling software application or system.

20. A computer processing system including at least one processor configured to perform the method of claim 1.

21. A non-transitory computer-readable medium storing instructions that, when executed by a computer, cause the computer to perform the method of claim 1.

22. The method of claim 1, wherein;

the measured fluid property for the first petroleum fluid sample is based on measurements of asphaltene onset pressure for the first petroleum fluid sample;

the tuning involves adjusting each of the plurality of adjustable parameters for one or more of the correlations based on matching at least one bulk fluid property measured for a plurality of different petroleum fluid samples and corresponding at least one bulk fluid property predicted by the computational model for the plurality of different petroleum fluid samples;

the first matching criterion is based on error or difference between measurements of asphaltene onset pressure for the plurality of different petroleum fluid samples and corresponding asphaltene onset pressure predicted by the computational model for the plurality of different petroleum fluid samples, wherein the error or difference error comprises a mean error of asphaltene onset pressure;

the binary interaction parameters of the computational model include at least binary interaction parameters between the pseudo-components that represents asphaltenes and light end components;

the method further comprises, after tuning the plurality of adjustable parameters of the correlations based on the measured fluid property for the first petroleum fluid sample, adjusting molecular weights for the pseudo-components representing asphaltenes of the first petroleum fluid sample until at least one additional matching criterion is satisfied; and the at least one additional matching criterion is based on error or difference between measurements of asphaltene onset pressure for a plurality of different petroleum fluid samples and corresponding asphaltene onset pressure predicted by the computational model for the plurality of different petroleum fluid samples, wherein the error or difference error comprises a mean error of asphaltene onset pressure.

23. The method of claim 1, wherein the tuning is repeated to adjust at least one of the plurality of adjustable parameters until molecular weights for asphaltenes for all of the different petroleum fluid samples fall within the predefined range of molecular weight of from 2200 g/mol to 4200 g/mol.

* * * * *